(12) United States Patent
Letendre

(10) Patent No.: US 6,729,417 B2
(45) Date of Patent: May 4, 2004

(54) DOUBLE SLEEVE SOIL TESTER

(76) Inventor: Marina Letendre, 201 - 1655 Nelson Street, Vancouver, B.C. (CA), V6G 1M4

( * ) Notice: Subject to any disclaimer, the term of this patent is extended or adjusted under 35 U.S.C. 154(b) by 0 days.

(21) Appl. No.: 10/134,379

(22) Filed: Apr. 30, 2002

(65) Prior Publication Data

US 2003/0201124 A1 Oct. 30, 2003

(51) Int. Cl.$^7$ ............................................... E21B 25/00
(52) U.S. Cl. ......................................... 175/20; 175/58
(58) Field of Search .................. 175/20, 58; 73/864.01, 73/864.51, 864.41

(56) References Cited

U.S. PATENT DOCUMENTS

| | | | | |
|---|---|---|---|---|
| 4,549,612 A | * | 10/1985 | Cushing | 175/20 |
| 5,121,643 A | * | 6/1992 | Voloudakis | 73/864.41 |
| 5,337,620 A | * | 8/1994 | Kalidini | 73/864.64 |
| 5,411,103 A | * | 5/1995 | Werner | 175/20 |

* cited by examiner

*Primary Examiner*—William Neuder

(57) ABSTRACT

A soil tester combination is provided that has an elongated rigid outer semi-cylindrical sleeve with a sharp narrowed outer sleeve end and a handle mounted on an opposite outer sleeve end, and a similar inner sleeve having a plurality of ledges bridging the walls of the inner sleeve at various depths.

5 Claims, 9 Drawing Sheets

DOUBLE SLEEVE SOIL TESTER

FIELD OF THE INVENTION

This invention relates to hand-operated soil testers that can be inserted into the soil for purposes of withdrawing soil samples in order to test soil moisture and other soil conditions.

BACKGROUND OF THE INVENTION

There exist soil tester tools that are adapted to be inserted down into the soil to be tested and that have ledges to catch soil at a plurality of depths for inspection after withdrawal of the soil test.

SUMMARY OF THE INVENTION

In this invention, a soil tester combination is provided that has an elongated rigid outer semi-cylindrical sleeve with a sharp narrowed outer sleeve end and a handle mounted on an opposite outer sleeve end, and a similar inner sleeve having a plurality of ledges bridging the walls of the inner sleeve at various depths.

The combination allows a gardener to insert the first, outer sleeve into a patch of soil to be sampled with less force required that would be to insert first the second, inner sleeve, because the first outer sleeve lacks the ledges which would block passage of the sleeve down into the soil. After the first, outer sleeve has been inserted, it can be withdrawn and the second, inner sleeve inserted, using the path already created by the first, outer sleeve, with little additional force required. After the second, inner sleeve has been inserted, it can be pulled up at once. If additional soil is desired, it can be re-inserted, and then the first, outer sleeve inserted behind it, pressing the second, inner sleeve's ledges into the adjacent soil wall, and causing soil from the various depths corresponding to the ledges to fall onto the ledges and retained upon the second, inner sleeve being withdrawn.

DETAILED DESCRIPTION

Figure 1:
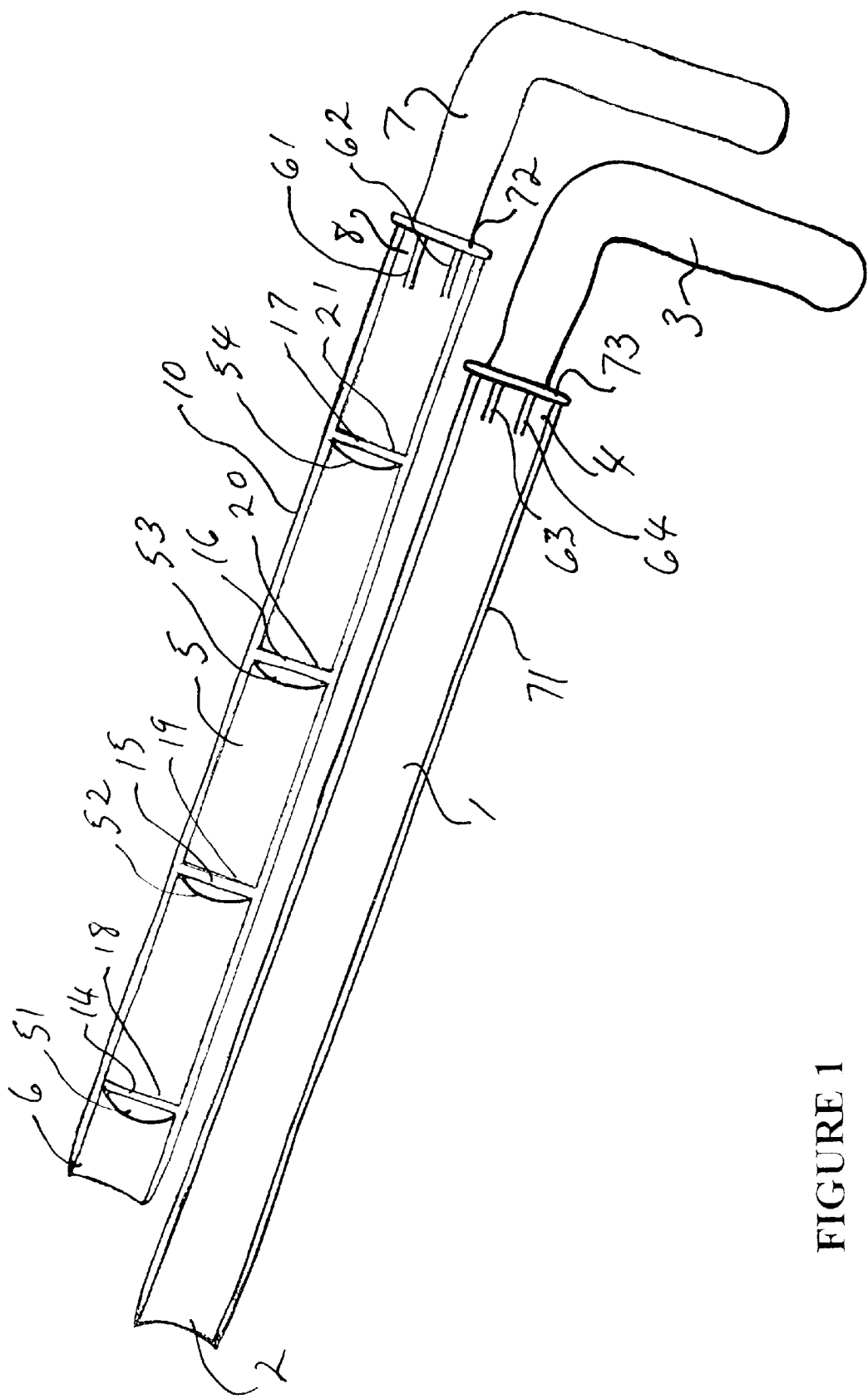
FIG. 1 is shows a front view of the first, outer sleeve and the second, inner sleeve of the soil tester of this invention.

Referring to FIG. 1, the soil tester comprises an elongated rigid semi-cylindrical first outer sleeve 1 with a narrowed sharpened outer sleeve end 2 and an outer sleeve handle 3 mounted on an opposite outer sleeve end 4, and a similar rigid semi-cylindrical inner sleeve 5 with a narrowed inner sleeve end 6 and an inner sleeve handle 7 mounted on an opposite inner sleeve 5 end 8.

The second inner sleeve body 10 has a plurality of ledges 14, 15, 16, 17 mounted therein at spaced intervals. The ledges can have sharpened exposed edges 18, 19, 20, 21 respectively, and can be angled such that the bottom portion (51, 52, 53, and 54 respectively) of each ledge is at a lower depth that the respective sharpened exposed edges.

The buttresses 61, 62, 63, and 64 strengthen the inner sleeve body 10 and the outer sleeve body 71 respectively to the inner sleeve handle plate 72 and the outer sleeve handle plate 73.

Figure 2:
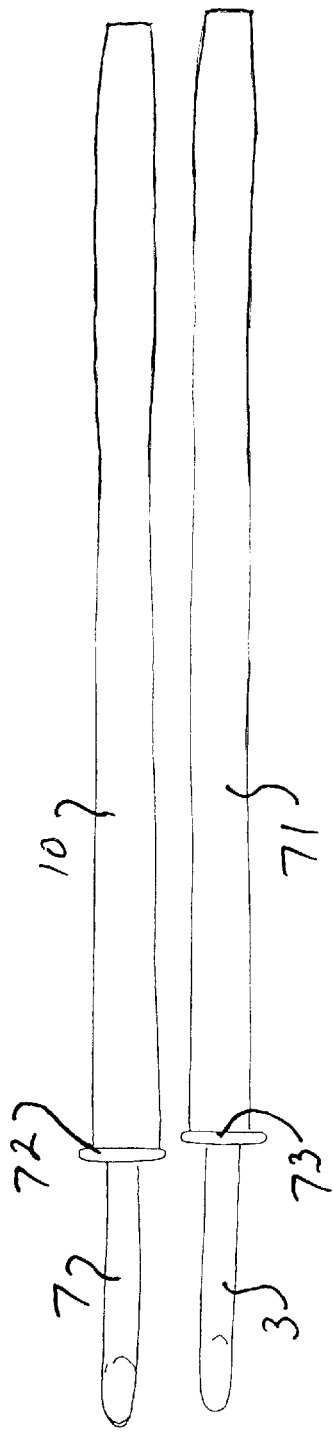
FIG. 2 is a side view of the first, outer sleeve and the second, inner sleeve of the soil tester of this invention.

Referring to FIG. 2 the handles 3 and 7 are joined to the handle plates 72 and 73, which in turn are joined to the inner sleeve body 10 and the outer sleeve body 71 respectively.

Figure 3:
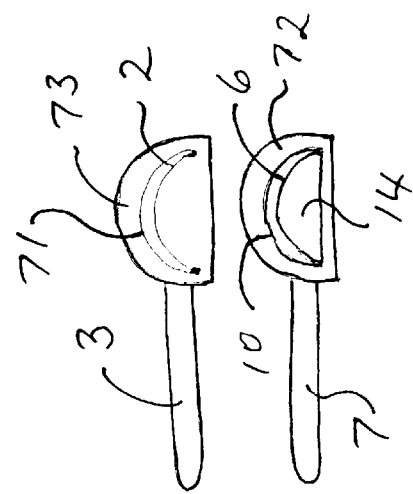
FIG. 3 is an end view of of the first, outer sleeve and the second, inner sleeve of the soil tester of this invention.
Figure 4A:
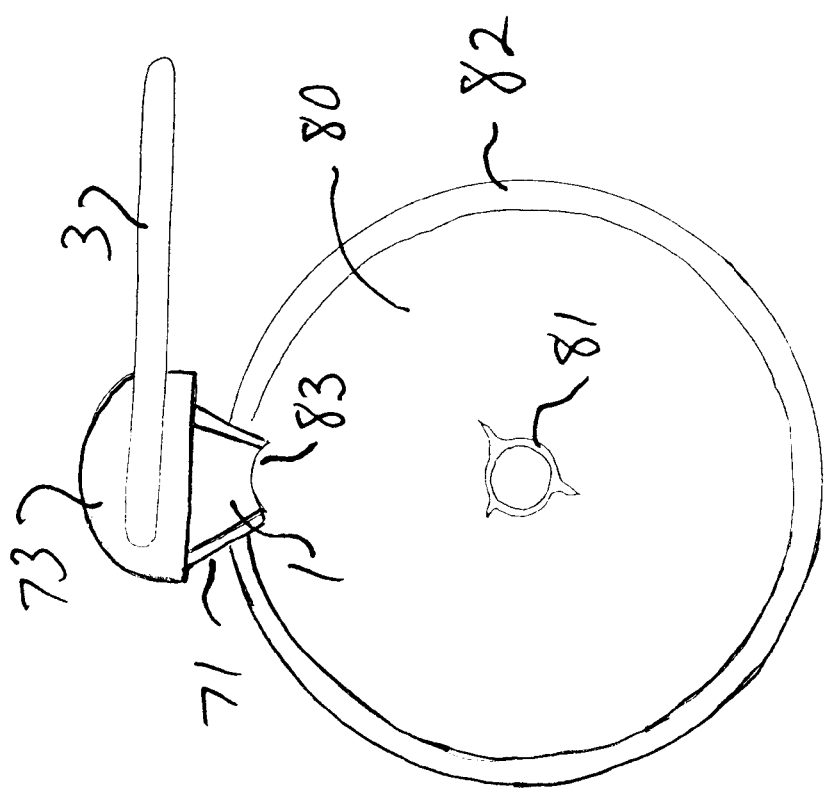
FIGS. 4A, 4B, and 4C are top views showing the soil tester being used.
Figure 4B:
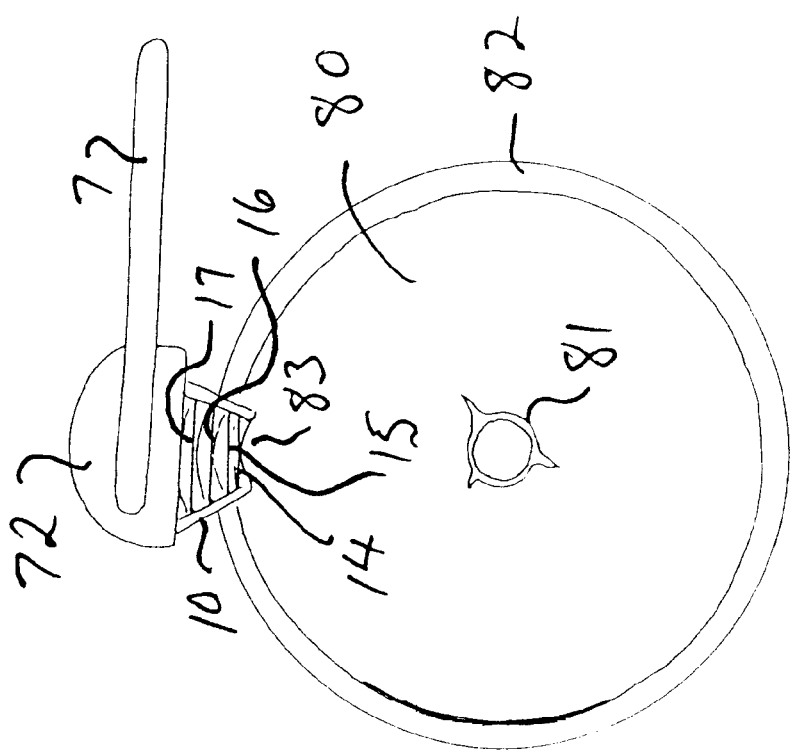
Figure 4C:
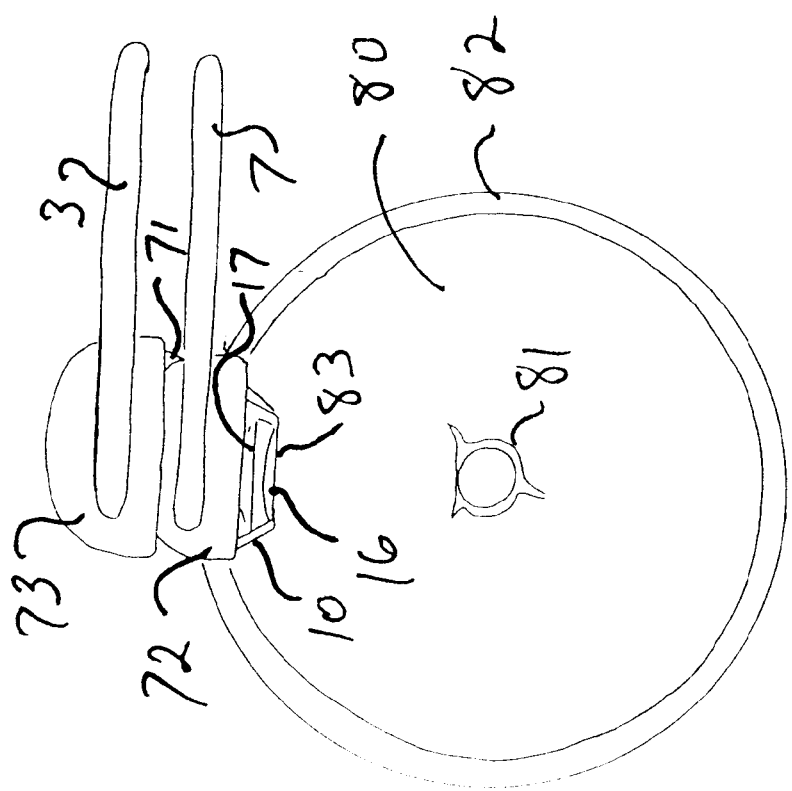
Figure 5A:
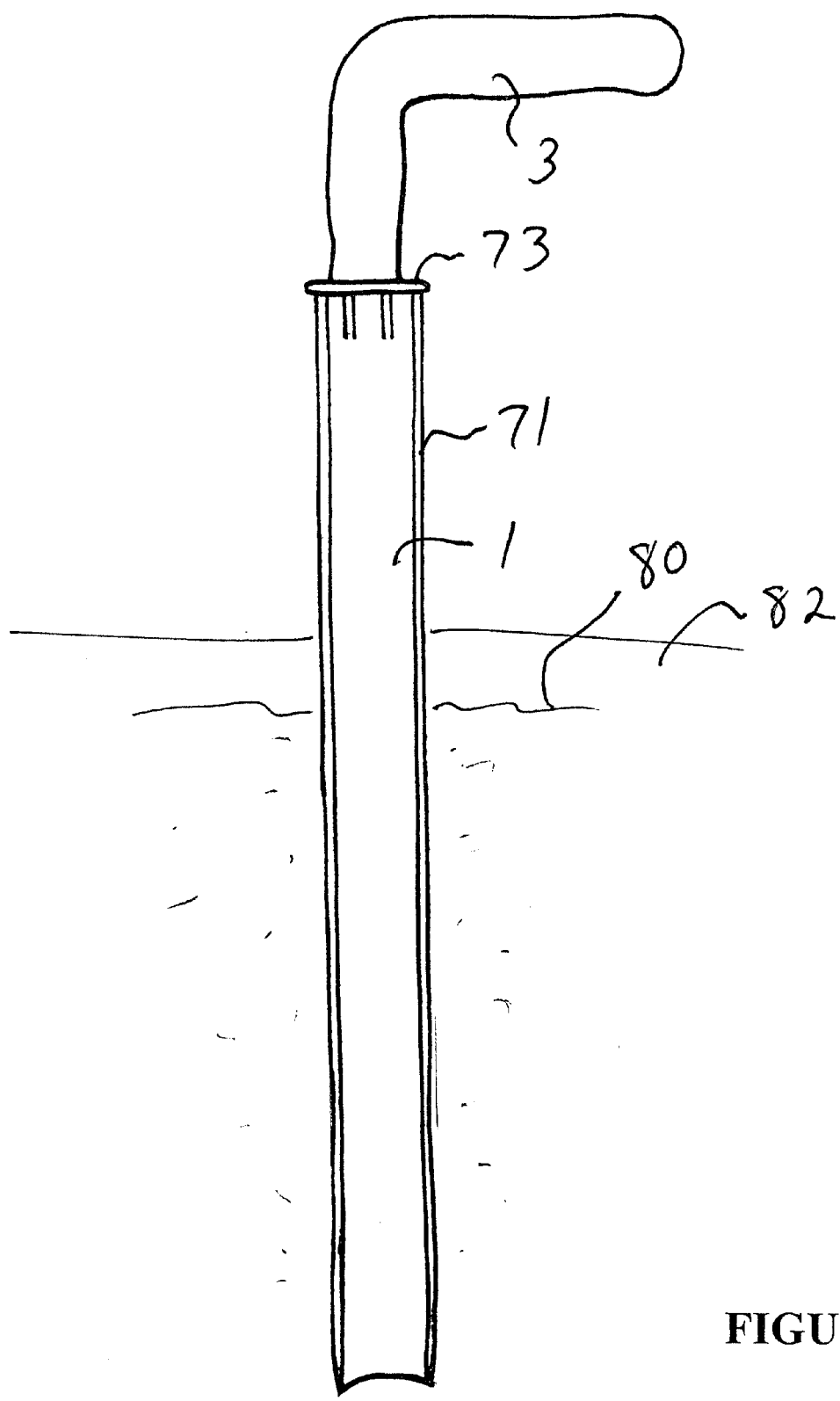
FIGS. 5A, 5B, 5C are cross-sectional sides views showing the soil tester being used.
Figure 5B:
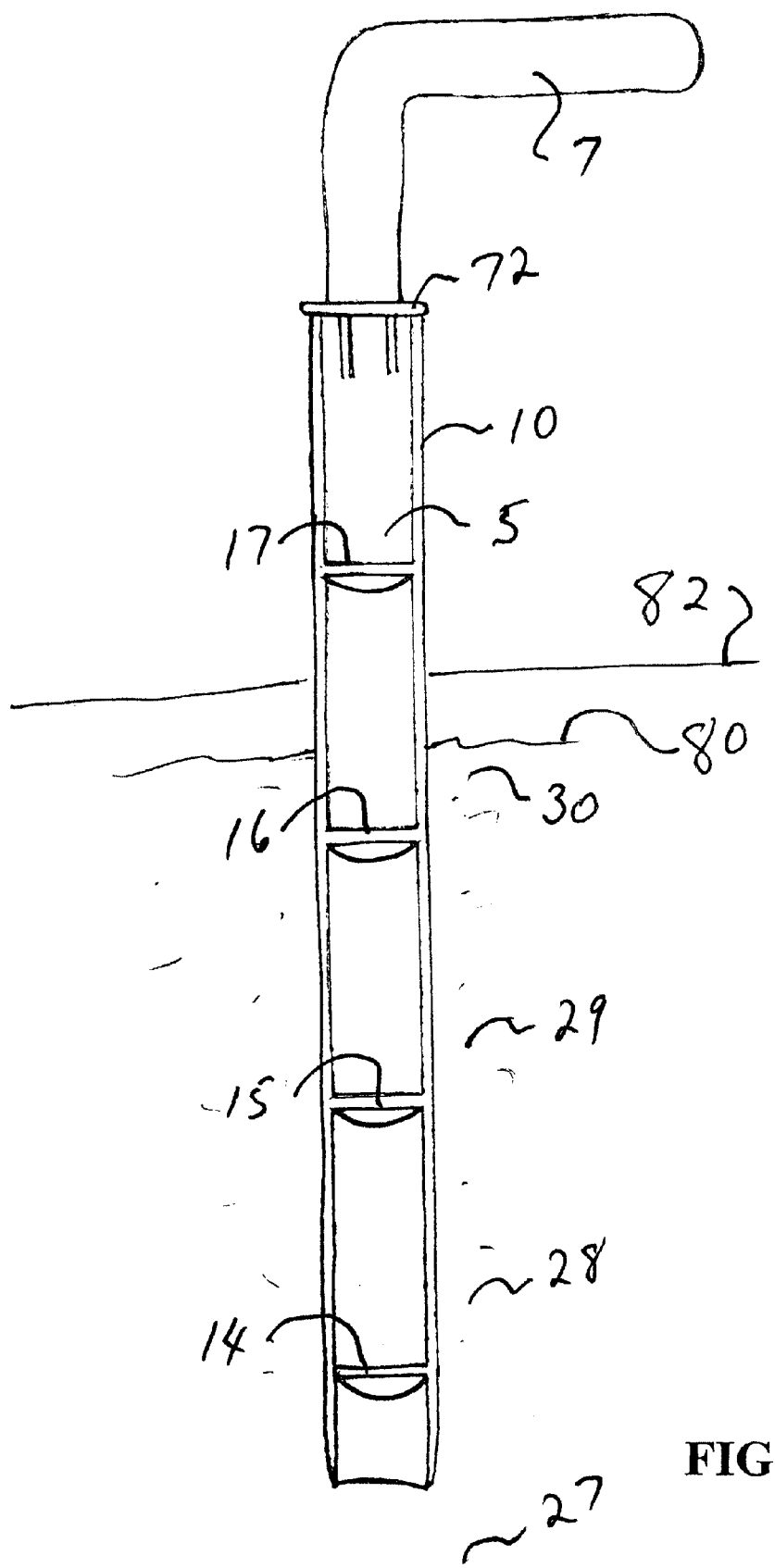
Figure 5C:
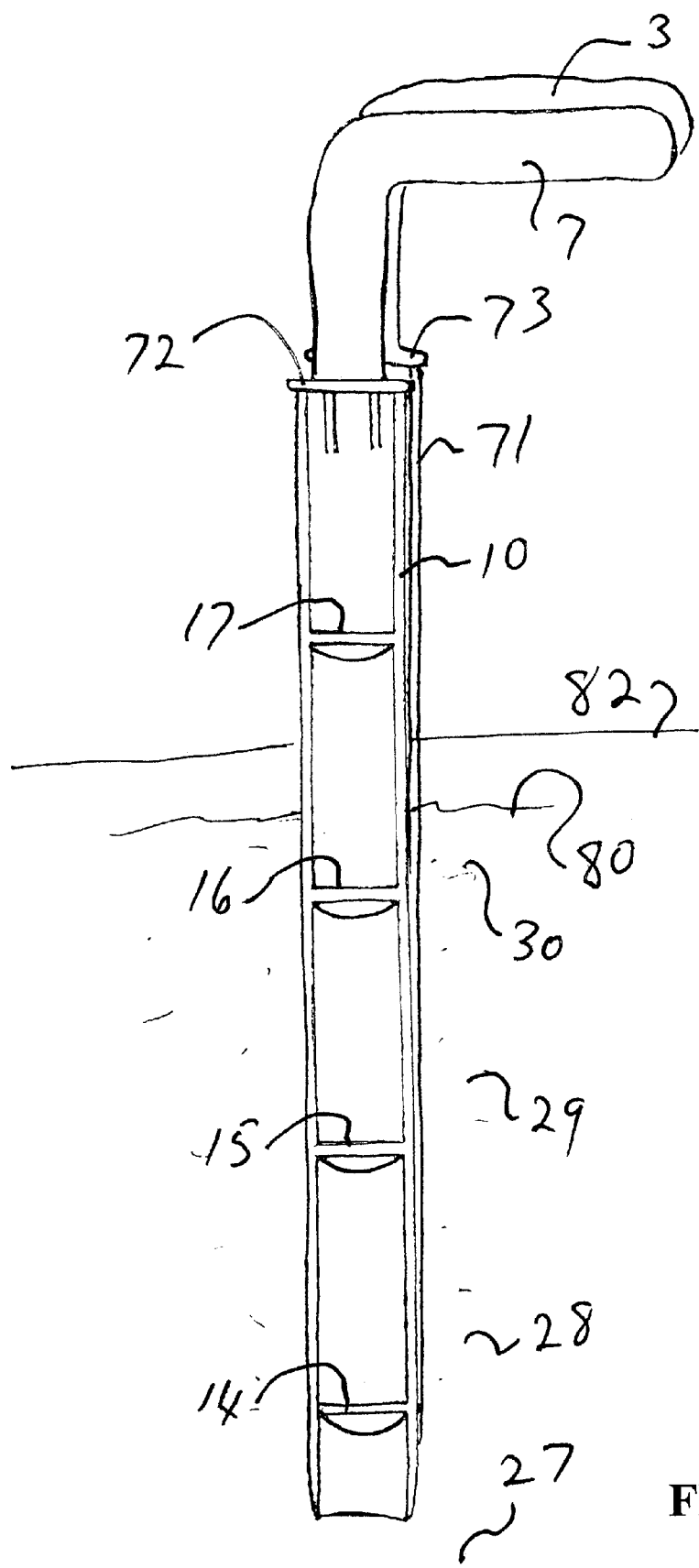
Figure 6:
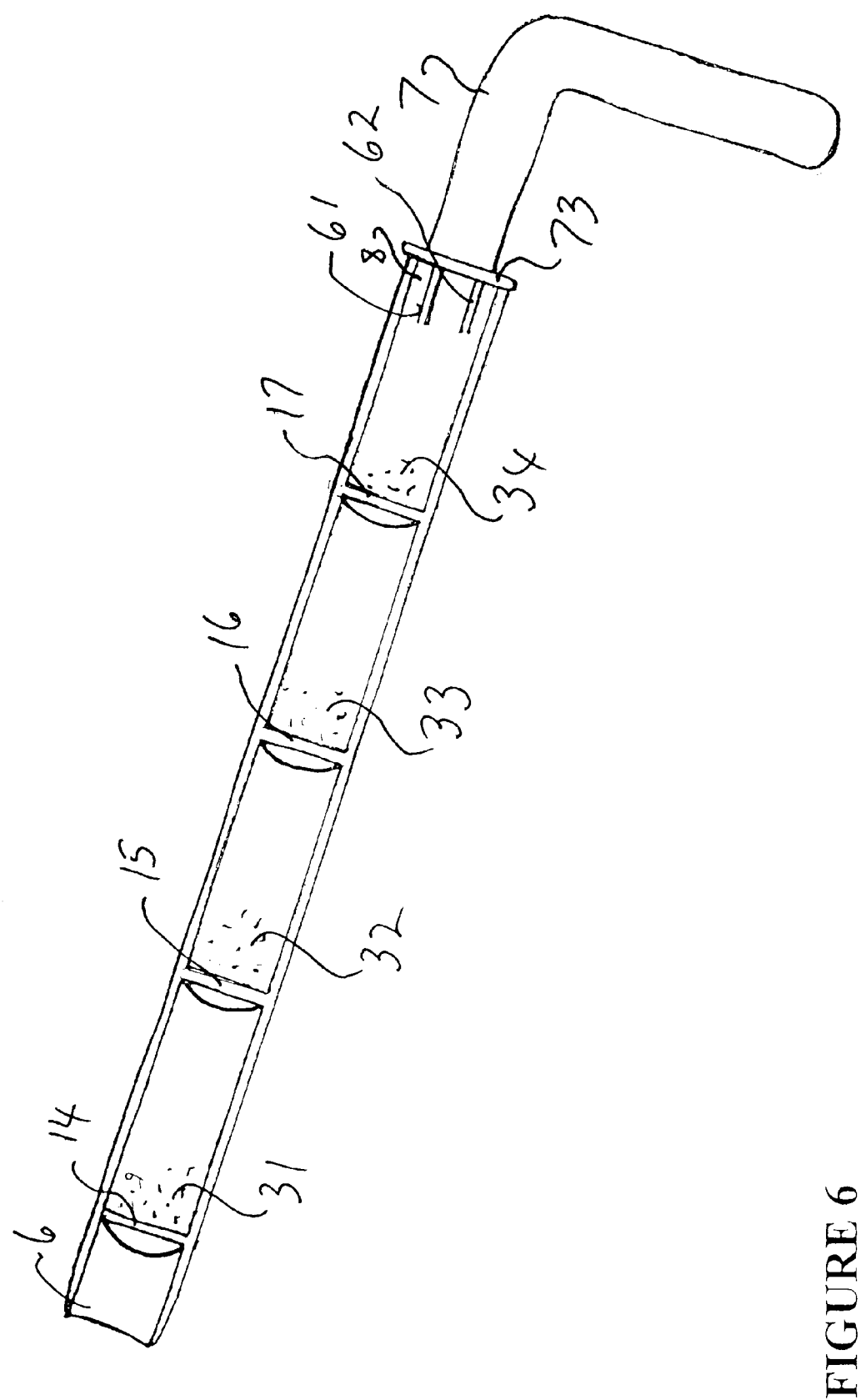
FIG. 6 is a front view of the second, inner sleeve with samples of soil extracted.

Referring to FIG. 3, the narrowed sharpened outer sleeve end 2 is on the outer sleeve body 71 which extends to the outer sleeve handle plate 73 to which the handle 3 is attached. Likewise, the narrowed sharpened inner sleeve end 6 is on the inner sleeve body 10 which extends to the inner sleeve handle plate 72 to which the handle 7 is attached. The bottom ledge 14 can be seen. Referring to FIGS. 4A and 5A, the first outer sleeve 1 is inserted to create a channel 83 down into the soil 80 adjacent to plant 81 in pot 82. It is then withdrawn and the second, inner sleeve 2 is inserted into the channel 83, as shown in FIGS. 4B and 5B. Lastly, the first, outer sleeve 1 can be re-inserted into the channel 83 behind the second, inner sleeve 2 in order to press the ledges of the second inner sleeve into the soil wall of channel 83, as shown in FIGS. 4C and 5C. The second inner sleeve can then be withdrawn to inspect the soil samples. Referring to FIG. 6, after extraction of the inner sleeve 5, the samples of soil 31, 32, 33, and 34 corresponding to soil depths 27, 28, 29, and 30 in FIG. 5 can be inspected. The within-described invention may be embodied in other specific forms and with additional options and accessories without departing from the spirit or essential characteristics thereof. The presently disclosed embodiment is therefore to be considered in all respects as illustrative and not restrictive, the scope of the invention being indicated by the appended claims rather than by the foregoing description, and all changes which come within the meaning and range of equivalence of the claims are therefore intended to be embraced therein.

What is claimed is:

1. A double sleeve soil tester combination, comprising:

a) an elongated rigid outer semi-cylindrical sleeve having a handle;

b) an inner sleeve having a plurality of ledges bridging an interior wall of the inner sleeve at various depths;

in which the elongated rigid outer semi-cylindrical sleeve has a sharpened end edge opposite from a handle end, the inner sleeve is similar to the elongated rigid outer semi-cylindrical sleeve but for the addition of the plurality of ledges bridging the interior wall of the inner sleeve at various depths, and the inner sleeve has a sharpened end edge opposite from the handle end.

2. The double sleeve soil tester combination of claim 1, in which the inner sleeve has a slightly narrowed end.

3. The double sleeve soil tester combination of claim 2, in which:

a) the elongated rigid outer semi-cylindrical sleeve has buttresses joining an outer sleeve body to a handle plate;

b) the inner sleeve has buttresses joining an inner sleeve body to a handle plate;
c) at least one of the plurality of ledges bridging the interior wall of the inner sleeve are angled down such that a bottom portion of that ledge is lower within the sleeve than a front edge of the ledge;
d) at least one of the plurality of ledges bridging the interior wall of the inner sleeve at various depths has a sharpened front edge.

4. The double sleeve soil tester combination of claim 1, in which the elongated rigid outer semi-cylindrical sleeve has buttresses joining an outer sleeve body to a handle plate.

5. The double sleeve soil tester combination of claim 1, in which the inner sleeve has buttresses joining an inner sleeve body to a handle plate.

* * * * *